United States Patent [19]
Ito et al.

[11] Patent Number: 6,124,126
[45] Date of Patent: Sep. 26, 2000

[54] COMPLEMENTARY DNA FOR RICE CHITINASE HAVING LYTIC ACTIVITY AGAINST MOULDS AND BACTERIA, AND VECTOR CONTAINING SAID COMPLEMENTARY DNA AND TRANSFORMANT

[75] Inventors: Yoshifumi Ito; Seung-Moon Park; Truong Nam Hai, all of Tsukuba, Japan

[73] Assignees: Director of National Food Research Institute, Ministry of Agriculture, Forestry and Fisheries, Tsukuba; Bio-oriented Technology Research Advancement Institution, Omiya, both of Japan

[21] Appl. No.: 09/178,610

[22] Filed: Oct. 26, 1998

[30] Foreign Application Priority Data

Apr. 20, 1998 [JP] Japan .................................. 10-123905

[51] Int. Cl.[7] ...................................................... C12N 9/24
[52] U.S. Cl. ...................... 435/200; 536/23.6; 536/23.2; 530/350; 530/370; 435/252.3; 435/252.8; 435/320.1; 435/69.1; 435/209
[58] Field of Search .................................... 435/200, 209, 435/320.1, 252.3, 252.8; 536/23.2, 23.6; 530/350, 370

[56] References Cited

PUBLICATIONS

Nagasaki et al. Rice Class III Chitinase Homologues Isolated by Random Cloning of Rice cDNAs, DNA Res. 4:379–385 Dec. 1987.

*Primary Examiner*—Rebecca E. Prouty
*Assistant Examiner*—Richard Hutson
*Attorney, Agent, or Firm*—Oblon, Spivak, McClelland, Maier & Neustadt, P.C.

[57] ABSTRACT

The present invention provides a complementary DNA for a rice chitinase having a lytic activity against moulds and a bacteria, a complementary DNA for a rice chitinase encoding a protein comprising an amino acid sequence described in SEQ ID NO: 1 in SEQUENCE LISTING, a plasmid vector containing said complementary DNA and a transformant having said plasmid vector. The present invention enables realization of a possibility of developing a recombinant crop plant having an acquired resistance against a wide range of pathogenic microorganisms by identifying a complementary DNA encoding a novel chitinase capable of lysing cell walls of both of moulds and bacteria and introducing the sequence thereof into a plant.

4 Claims, 2 Drawing Sheets

COMPLEMENTARY DNA FOR RICE CHITINASE HAVING LYTIC ACTIVITY AGAINST MOULDS AND BACTERIA, AND VECTOR CONTAINING SAID COMPLEMENTARY DNA AND TRANSFORMANT

FIELD OF THE INVENTION

The present invention relates to a complementary DNA for a rice chitinase having a lytic activity against moulds and bacteria, and a plasmid vector containing said complementary DNA and a transformant.

BACKGROUND OF THE INVENTION

Chitinases are enzymes that hydrolyze chitin which is a constituent of exoskeleton of insects and crustaceans as well as cell walls of moulds, and widely distributed in microorganisms and plants.

Plants have 5 kinds of chitinases classified as classes I–V, amongst those classes I, II, IV and V chitinases have an ability of decomposing cell walls of moulds but lack an ability of decomposing cell walls of bacteria. On the other hand, the class III chitinase has an ability of decomposing cell walls of bacteria but lacks an ability of decomposing cell walls of moulds.

The present invention relates to a complementary DNA for a novel rice chitinase having a lytic activity against both of moulds and of bacteria as well as to utilization thereof.

Agriculture sustains a great loss by a decrease in yield of harvest because of an infection by plant pathogenic microorganisms. As a means for prevention of the infection and inhibition of enlargement of the infection by these microorganisms, spraying of germicides has been carried out.

In recent years, however, there is a demand for the development of techniques for preventing and exterminating against the infection of pathogens without relying on chemical substances, because of anxiety for influences to the environment and to the human body by these germicides.

Plants have their unique preventing and exterminating mechanisms against invading pathogenic microorganisms. Specifically, when plants become aware of infection by a pathogenic microorganism, they protect themself or their plant bodies from the infection by producing antimicrobial agents such as a compound called phytoalexin, pathogenicity related protein (PR protein) and so on.

The PR protein includes, as enzymes having the clearest action mechanism against microorganisms, chitinases and β-1, 3-glucanases that hydrolyze chitin and β-1, 3-glucan that constitute cell walls of moulds.

As described above, plants have 5 kinds of chitinases classified as classes I–V, amongst those classes I, II, IV and V chitinases have an antifungal activity inhibiting growth of moulds. These chitinases act on the growing of hypha at which synthesis of cell wall is particularly active. As the result, the growing cells are destructed and extension of hypha is inhibited.

Amongst them, the classes I and IV enzymes having a chitin binding region have particularly high antifungal activity, and are attracting attention as a gene to be introduced for development of crop plants being resistant against the pathogenic moulds.

Under such circumstances, researches have been conducted to develop crop plants being resistant against the pathogenic moulds by introducing a complementary DNA for a chitinase into the plants.

While, however, the chitinase encoded by said introduced gene can certainly decompose the cell walls of the pathogenic moulds, they do not have a lysozyme activity decomposing the cell walls of bacteria. Therefore, even if a chitinase encoded by said gene is introduced into the crop plants, the plants are not provided with the resistance against the pathogenic bacteria. Accordingly, such a character is insufficient for creating resistant crop plants.

On the other hand, it has long been known that plants have an enzyme having a lysozyme activity. In addition, it has also been known that hevamine existing in latex of rubber tree and some class III chitinase have a lysozyme activity lysing the cell walls of bacteria. No report, however, has been presented for a complementary DNA and a gene relating to hevamine. In addition, no complementary DNA for a chitinase having a lysozyme activity has been known.

Thus, until now, no complementary DNA for a chitinase having both of the antifungal activity and the lysozyme activity has been known; i.e. it has not been demonstrated by expressing a protein that a complementary DNA encodes a chitinase having both of the antifungal activity and the lysozyme activity.

The purpose of the present invention is to demonstrate a possibility of developing a recombinant crop plant having an acquired resistance against a wide range of pathogenic microorganisms by identifying a complementary DNA encoding a novel chitinase capable of lysing cell walls of both moulds and bacteria and introducing the sequence thereof into a plant.

After conducting extensive studies in order to attain the above purpose, the present inventors have successfully isolated from rice plant a complementary DNA encoding a chifinase having a lysing activity to both of the moulds and bacteria by a method described below.

Thus, the present inventors have determined the complete nucleotide sequence of a complementary DNA contained in S4960 clone isolated by the Rice Genome Project, and have revealed that said clone contains a complementary DNA having 1,109 bp encoding a protein having a molecular weight of 32,260 Dalton and comprising 305 amino acid residues. They have considered that said protein is probably a chitinase because the amino acid sequence thereof have 68% homology with the sequence of hevamine which is the class III chitinase contained in the latex of rubber tree.

Subsequently, in order to construct an expression system for said protein, they have conducted researches for constructing the expression system using several kinds of microorganisms as hosts. As the result, they discovered that said protein could be efficiently expressed with secretion when *Pichia pastoris,* a kind of yeast, is used as the host.

In addition, they have purified said protein produced in *Pichia pastoris* and demonstrated that the purified protein is a chitinase capable of decomposing glycol chitins and chito-oligosuccharides. Furthermore, they have demonstrated that the purified protein exhibit an antifungal activity against *Trichoderma reesei,* a mould, and simultaneously, a lysozyme activity lysing cells of *Micrococcus lysodeikticus,* a bacterium. The present invention has been completed based on these findings.

SUMMARY OF THE INVENTION

Thus, the first aspect of the present invention is directed to a complementary DNA for a rice chitinase having a lytic activity against moulds and bacteria.

The second aspect of the present invention is directed to a complementary DNA for a rice chitinase encoding a protein comprising an amino acid sequence described in SEQ ID NO: 1 in SEQUENCE LISTING.

The third aspect of the present invention is directed to a plasmid vector containing the complementary DNA for a rice chitinase.

The fourth aspect of the present invention is directed to a transformant having the plasmid vector.

BRIEF DESCRIPTION OF THE DRAWING

In FIG. 3, A is a photograph showing growth of *Trichoderma reesei* IF031329 around a pulp disc impregnated with bovine serum albumin; and B is a photograph showing growth of *Trichoderma reesei* IF031329 around a pulp disc impregnated with the purified rice chitinase.

DETAILED DESCRIPTION OF THE INVENTION

Figure 1:
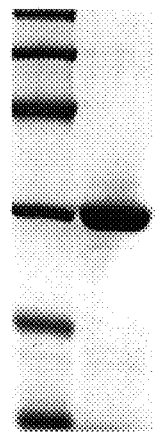
FIG. 1 is a photograph showing the result of analysis of the purified rice chitinase by SDS-polyacrylamide gel electrophoresis.

The present invention is described below in more detail.

The complementary DNA for a rice chitinase according to the present invention is a part of a DNA sequence derived from rice. For the purpose of obtaining a complete length of complementary DNA encoding a plant class III chitinase having an antifungal activity and a lysozyme activity, the present inventors have conducted a Blast homology investigation (Altschul, S. F., Madden, T. L., Schaffer, A. A., Zhang, J., Zhang, Z., Miller, W. and Lipman, D. J., Nucleic Acids Res., 25, 3389–3402, 1997) on a DNA data base in which many partial sequences of complementary DNA were registered by the Rice Genome Project (RGP, Japan).

As the result, they have dound that a partial sequence (405 bp) of the clone S4960 has 59% homology with the complementary DNA for the tobacco class III chitinase (Lawton, K., Ward, E., Payne, G., Moyer, M. and Ryals, J., Plant Mol. Biol., 19, 735–743, 1992).

Subsequently, they have determined the complete base sequence of the complementary DNA contained in the clone S4960. The determination can be attained by a routine method. For example, said complementary DNA can be subjected to a sequence reaction with a di-primer cycle sequencing kit manufactured by Perkin-Elmer using as a template a plasmid DNA prepared by Flex-prep plasmid purification kit manufactured by Pharmacia. In addition, the DNA sequence can be determined using a DNA sequencer (Model ABI377, manufactured by Perkin-Elmer).

The plasmid DNA used as a template can also be prepared by the alkali-SDS method (Sambrook, J., Fritsch, E. F. and Maniatis, T., Molecular Cloning, A Laboratory Manual, Cold Spring Harbor Laboratory Press, New York, 1989).

Further, the base sequence can also be determined by a method of Sanger (Sanger, F., Nicklen, S. and Coulson, A. R., Proc. Natl. Acad. Sci. USA, 74, 5463–5467, 1977) or a method of Maxam-Gilvert (Maxam, A. M. and Gilvert, W., Methods Enzymol., 65, 499–560, 1980).

As the result, it was revealed that the clone S4960 contained a complementary DNA of 1,109 bp and was estimated that said clone was encoded a protein having a molecular weight of 32,260 Dalton comprising 305 amino acid residues (see SEQ ID NO: 1 in SEQUENCE LISTING). The protein shown in SEQ ID NO: 1 is listed separately in the Sequence Listing as SEQ ID NO: 6.

This complementary DNA of 1,109 bp is the complementary DNA for a rice chitinase according to the present invention.

The fact that the complementary DNA for rice chitinase according to the present invention encodes a chitinase can be clearly understood by the fact that the result of homology investigation for an amino acid sequence of a protein expected from the sequence of said DNA indicates 68% homology with the hevamine which is a chitinase in a rubber tree (Jekel, P. A., hartmann, B. H. and Beintema, J. J., Eur. J. Biochem., 200, 123–130, 1991).

A plasmid containing the complementary DNA of 1,109 bp, the complete base sequence of which was determined, was transformed into *Escherichia coli* DH5α (manufactured by Bethesda Research Laboratories).

The transformation can be conducted according to the routine method, such as for example, a method of Inoue et al. (Inoue, H., Nojima, H and Okayama, H., Gene, 96, 23–28, 1990), the calcium chloride method (Cohen, S. N., Chang, A. C. Y. and Hsu, L., Proc. Natl. Acad. Sci. USA, 69, 2110–2114, 1972), the electroporation method (Kin-ichiro Miura et al., Ed., Shinkisoseikagakujikkenho (Novel Basic Biochemical Experiment Method), Gene Engineering, published by Maruzen, 1988) and so on.

The transformed *Escherichia coli* was deposited in the National Institute of Bioscience and Human-Technology Agency of Industrial Science and Technology, 1—3, Higashi 1-chome, Tsukuba-shi, Ibaraki-ken, 305–8566, JAPAN, under an accession number of FERM BP-6286.

It is to be appreciated that the methods described above are mere examples and a complementary DNA having the same sequence as that in the present invention can be obtained from a rice complementary DNA library by other methods including, for example, the colony or plaque hybridization method (Sambrook, J., Fritsch, E. F. and Maniatis, T., Molecular Cloning, A Laboratory Manual, Cold Spring Harbor Laboratory Press, New York, 1989) using a complementary DNA of S4960 as the probe.

Using the complementary DNA according to the present invention, a chitinase encoded thereby was produced and its antifungal activity and cell wall-lysing activity was demonstrated by the following procedure.

First, a matured enzyme region of 30th–305th amino acid in the amino acid sequence (see SEQ ID NO: 1 in SEQUENCE LISTING) was amplified from said clone plasmid by the PCR method (Methods in Molecular Biology, vol. 15, 1993) with KOD DNA polymerase (manufactured by Toyobo) using two synthetic oligonucleotides (manufactured by Hokkaido System Service), i.e., Oligo E-1 (see SEQ ID NO: 2 in SEQUENCE LISTING) and Oligo E-2 (see SEQ ID NO: 3 in SEQUENCE LISTING). The amplified DNA fragments were ligated to a vector plasmid pET-22b(+) (manufactured by Novagen) to give a plasmid pOIS5.

Next, a PCR reaction (with KOD DNA polymerase) was conducted using Oligo P-1 (see SEQ ID NO: 4 in SEQUENCE LISTING, manufactured by Hokkaido System Service) and Oligo P-2 (see SEQ ID NO: 5 in SEQUENCE LISTING, manufactured by Hokkaido System Service) as the primers, and using the plasmid OIS5 DNA as the template. The amplified DNA fragments were cloned into a plasmid vector pPIC9 (manufactured by Invitrogen) to give a recombinant plasmid pOIS9. Using the electroporation technique, pOIS9 was transformed into a histidine-requiring strain of *Pichia pastoris* G115 (manufactured by Invitrogen) to give a transformant *Pichia pastoris* IIIa having said complementary DNA in its chromosome.

The expression of the complementary DNA for a rice chitinase according to the present invention can be confirmed by culturing the transformant *Pichia pastoris* and identifying the amino acid sequence of the enzyme produced by said yeast or by measuring the chitinase activity.

The complementary DNA according to the present invention encodes a novel (plant class III) chitinase which exhibit lytic effect not only against moulds but also against bacteria. Heretofore, there has been no report concerning a complementary DNA encoding a chitinase having a lysozyme activity lysing cell walls of bacteria. In addition, a chitinase having both of antifungal activity and lysozyme activity have been found for the first time by the present invention.

Moreover, an expression system for microorganism efficiently producing a plant chitinase having said activities has not been established before. The complementary DNA for a rice chitinase according to the present invention provides a possibility of developing a recombinant crop plant having an acquired resistance against a wide range of pathogenic microorganisms.

The present invention provides a complementary DNA encoding a rice chitinase. The rice chitinase encoded by the complementary DNA is an enzyme having a lytic effect not only against moulds but also against bacteria. Heretofore, there has been no report concerning a complementary DNA encoding a chitinase having a lysozyme activity lysing cell walls of bacteria. In addition, a chitinase having both of antifungal activity and lysozyme activity has not been found until now.

Moreover, the present invention provides a plasmid and transformant into which the complementary DNA for the rice chitinase is integrated. By utilizing them, development of a recombinant crop plants having an acquired resistance against a wide range of pathogenic microorganisms becomes possible.

EXAMPLES

The present invention will now be described in more detail with reference to the appended Examples, which should not be construed as a limitation upon the scope of the present invention.

Example 1

(1) Obtaining of clone S4960

A possibility that a rice complementary DNA library made by the Rice Genome Project would contain a clone encoding a class III chitinase was investigated. A Blast homology investigation (Altschul, S. F., Madden, T. L., Schaffer, A. A., Zhang, J., Zhang, Z., Miller, W. and Lipman, D. J., Nucleic Acids Res., 25, 3389–3402, 1997) was carried out on DNA sequences registered in the DNA data base using a sequence of a complementary DNA for tobacco class III chitinase (Lawton, K., Ward, E., Payne, G., Moyer, M. and Ryals, J., Plant Mol. Biol., 19, 735–743, 1982). As the result, it was found that sequences having a significant homology contained two clones isolated by the Rice Genome Project.

Therefore, one of these clones, S4960, was obtained from the Rice Genome Project. The partial sequence (405 bp) of the complementary sequence of the clone S4960 has 59% homology with that of the tobacco class III chitinase.

(2) Characterization of Base Sequence of the Complementary DNA Contained in clone S4960

A sequence reaction was carried out with a di-primer cycle sequencing kit manufactured by Perkin-Elmer using as a template a plasmid DNA prepared by purifying said clone DNA with Flex-prep plasmid purification kit manufactured by Pharmacia. The base sequence was determined using a DNA sequencer (Model ABI377, manufactured by Perkin-Elmer).

As the result, it was revealed that said clone contained a complementary DNA of 1,109 bp and was estimated that said clone was encoded a protein having a molecular weight of 32,260 Dalton comprising 305 amino acid residues (see SEQ ID NO: 1 in SEQUENCE LISTING).

The result of Blast homology investigation (Altschul, S. F., Madden, T. L., Schaffer, A. A., Zhang, J., Zhang, Z., Miller, W. and Lipman, D. J., Nucleic Acids Res., 25, 3389–3402, 1997) on an amino acid sequence of the expected protein indicated 68% homology with hevamine which is a chitinase in a rubber tree (Jekel, P. A., Hartman, B. H. and Beintema, J. J., Eur. J. Biochem., 200, 123–130, 1991).

(3) Examination of Production of the Protein Encoded by the Complementary DNA in *Pichia pastoris*.

Previously, expression of the protein encoded by the complementary DNA contained in S4960 was attempted in several host-vector systems of *Excherichia coli* under various conditions. The expressed protein, however, formed inclusion bodies in the form of an insoluble protein.

Then, expression was attempted in *Pichia pastoris* (manufactured by Invitrogen), a kind of yeast which was an eukaryotic microorganism.

(a) Attachment of histidine-tag

In order to attach a histidine-tag at the C-terminal of the mature protein consisting of 30th–305th residues in the amino acid sequence (see SEQ ID NO: 1 in SEQUENCE LISTING) of the protein encoded by the complementary DNA contained in S4960, the S4960 clone plasmid was amplified by the PCR method (Methods in Molecular Biology, vol. 15, 1993) with KOD DNA polymerase (manufactured by Toyobo) using two synthetic oligonucleotides (manufactured by Hokkaido System Service), i. e., Oligo E-1 (see SEQ ID NO: 2 in SEQUENCE LISTING) and Oligo E-2 (see SEQ ID NO: 3 in SEQUENCE LISTING). The reaction was conducted under the condition recommended by Toyobo.

(b) Preparation of a recombinant plasmid pOIS5

The amplified DNA fragments were cleaved with restriction enzymes NcoI and HindIII, and the products were ligated in a vector plasmid pET-22b(+) (manufactured by Novagen) cleaved with the same restriction enzymes using a DNA ligation kit (Ver. 1) manufactured by Takara.

The ligated plasmid DNA was transformed into *Escherichia coli* DH5 α (manufactured by Bethesda Research Laboratories) by a method of Inoue et al. (Inoue, H., Nojima, H and Okayama, H., Gene, 96, 23–28, 1990).

A plasmid DNA was prepared from the transformant by the alkali-lysis method (Sambrook, J., Fritsch, E. F. and Maniatis, T., Molecular Cloning, A Laboratory Manual, 2nd ed. Cold Spring Harbor Laboratory Press, New York, 1989) and analyzed by restriction enzymes. Thus, the desired recombinant plasmid pOIS5 was obtained. Upon DNA sequencing as described above, it was confirmed that the pOIS5 had the correct nucleotide sequence.

(c) Preparation of a recombinant plasmid pOIS9

Next, in order to produce a mature protein having attached histidine-tag in *Pichia pastoris,* a PCR reaction (with KOD DNA polymerase) was conducted using Oligo P-1 (see SEQ ID NO: 4 in SEQUENCE LISTING, manufactured by Hokkaido System Service) and Oligo P-2 (see SEQ ID NO: 5 in SEQUENCE LISTING, manufactured by Hokkaido System Service) having a restriction sites SnaB1 and NotI as the primers and using the plasmid pOIS5 DNA as the template.

After confirming the base sequence of the amplified DNA fragments, they were cleaved with SnaB1 and NotI. Then, they were cloned in-frame into a plasmid vector pPIC9 (manufactured by Invitrogen) such that an open reading frame was continued between said restriction sites positioned at the C-terminal of a signal sequence of α-factor in said vector. In this way, a recombinant plasmid pOIS9 was obtained.

(d) Preparation of a transformant *Pichia pastoris* IIIa

Using the electroporation technique, pOIS9 was transformed into a histidine-requiring strain of *Pichia pastoris* G115 (His-; manufactured by Invitrogen) after cleaving with a restriction enzyme BglII. The electroporation was conducted under conditions described in a manual of Invitrogen. Then, histidine-prototrophic strains were selected on MD minimum agar medium (1.34% yeast nitrogen base, $4\times10^{-5}$% biotin, 1% glucose, 1.5% agar) to give the desired transformant *Pichia pastoris* IIIa.

(e) Induction of purified chitinase from the transformant *Pichia pastoris* IIIa Induction of the chitinase was carried out according to the manual of Invitrogen.

Briefly, first, *Pichia pastoris* was cultured with shaking in 50 ml of BMGY medium (1% bacto yeast extract, 2% peptone (manufactured by Sigma), 100 mM potassium phosphate, pH 6.0, 1.34% bacto yeast nitrogen broth, $4\times10^{-5}$% biotin, 1% glycerol) at 30° C. for 20 hours.

After the culture, cells were collected by centrifugation (3000×g, 5 minutes), re-suspended in 50 ml of BMMY medium (having the same composition as that of BMGY except that it contains methanol in place of glycerol) and cultured again with shaking at 30° C. for 24 hours.

(f) Purification of the chitinase (affinity column chromatography)

It was clearly shown by a preliminary experiment that the expressed protein was produced with secretion in the medium. Therefore, a supernatant from the culture was applied directly onto a nickel column and the protein was purified by affinity column chromatography making use of the fact that said protein was adsorbed to the nickel column through the intervention of 6 histidine residues (His-tag) at the C-terminal thereof.

Specifically, a supernatant obtained by centrifuging the culture at 3000×g for 5 minutes was applied onto a His-trap column (volume of the culumn: 1 ml) manufactured by Pharmacia. The column was washed with 5 ml of 20 mM phosphate buffer (pH: 7.5) containing 0.5 M NaCl and 10 mM imidazole and then the protein was eluted with 5 ml of 20 mM phosphate buffer (pH: 7.5) containing 0.5 M NaCl and 500 mM imidazole.

(g) Electrophoresis of the purified chitinase and amino acid sequencing of N-terminal.

In order to confirm that the protein was purified to a sufficient purity by the above procedure, the protein was analyzed by the two kinds of electrophoresis including SDS polyacrylamide gel electrophoresis and isoelectric focusing as well as amino acid sequencing of the N-terminal.

First, SDS polyacrylamide gel electrophoresis was conducted according to a method of Laemmli (Nature, 227, 680–685, 1970) using ReadyGel J (12.5% polyacrylamide) manufactured by Biorad. Briefly, 3 μg of said purified protein was subjected to the electrophoresis after treating with 10 μl of a sample buffer (Laemmli, U. K., Nature, 227, 680–685, 1970). The proteins were stained with Coomassie Brilliant Blue. A photograph of the result of migration is shown in FIG. 1.

In FIG. 1, molecular weight markers are on the left lane and the purified rice chitinase is on the right lane.

As is evident from FIG. 1, only a protein band corresponding to a molecular weight of 30,000 Daltons, which agrees with the estimated molecular weight of the protein 30,931, was detected for the purified fraction in the stained gel.

From the above fact, the molecular weight of the protein was calculated as 30,000 Daltons.

Next, 1 μg of the purified protein was charged on PhastGel IEF3-9 gel manufactured by Pharmacia and subjected to isoelectric focusing with PhastSystem electrophoresis apparatus manufactured by Pharmacia. Proteins on the gel were stained according to a method recommended by Pharmacia. The result is shown in FIG. 2.

Figure 2:
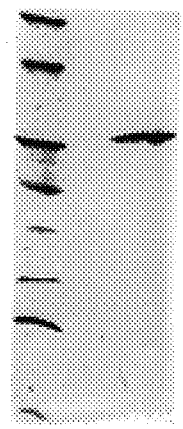
FIG. 2 is a photograph showing the result of analysis of the purified rice chitinase by isoelectric focusing.

In FIG. 2, isoelectric point marker proteins are on the left lane and the purified rice chitinase is migrated on the right lane.

Based on the result in FIG. 2 and a calibration curve prepared from length of migration of isoelectric point marker proteins, the isoelectric point of the rice chitinase was calculated to be 8.2.

In addition, the amino acid sequence of N-terminal of the purified protein was analyzed by an automatic protein sequencer (Model G1000A. manufactured by Hewlett Packard).

As the result, it was revealed that the amino acid sequence of N-terminal of said purified protein started with a C-terminal sequence Glu-Ala-Glu-Ala-Tyr at a cleavage site of the signal sequence in α-factor, followed by Val which was changed from Ala at the original 29th amino acid when SnaBI site was introduced in order to ligate the DNA fragment encoding said protein behind the base sequence of a α-factor, and further by Gly-Asp-Ile-Ala which is an amino acid sequence of said protein.

Upon analysis of this amino acid sequence, no amino acid except the amino acids contained in the sequence of said protein was detected.

From the above results, it was concluded that said protein was purified sufficiently.

(h) Measurement of the chitinase activity

Then, experiments for demonstrating that said protain has a chitinase activity were conducted using the purified protein.

The protein was added to 0.1 M Tris-HCl buffer (pH: 8.4) containing 0.2% glycol chitin (Imoto, T. and Yagishita, K., Agric. Biol. Chem., 35, 1154–1156, 1971) which was routinely used in a measurement of chitinase activity, and the mixture was incubated at 37° C.

Reducing sugars in the solution was measured according to a method of Monrea and Reese (Can. J. Microbiol., 15, 689–696, 1969). It was observed that the reducing sugars increased depending on the reaction period and the amount of the protein added.

The enzymatic analysis of the chitinase activity of said protein showed the following results:

Molecular weight: 30,000 Daltons (Experimental); 30,931 Daltons (Calculated)

Isoelectric point: 8.2 (Experimental)

Amino acid sequence of N-terminal: Glu-Ala-Glu-Ala-Tyr-Val-Gly-Asp-Ile-Ala

Optimal pH: 8.4 (glycol chitin)

3.0–5.0 (lysozyme activity)

Km for glycol chitin: 0.4 mg/ml

Vmax for the same: 5.2 units/mg

It was found that the optimal pH for the reaction was 8.4, and Km and Vmax for glycol chitin were 0.4 mg/ml and 5.2 units/mg protein, respectively. In addition, the purified protein decomposed N-Acetyl-hexa-D-glucosamine to N-Acetyl-di-D-glucosamine.

(i) Measurement of antifungal activity of the protein

The antifungal activity of said purified protein was assayed according to a method of Roberts and Selitrennikoff (J. Gen. Microbiol., 134, 169–176, 1988) using a strain Trichoderma reesei IFO31329 as the indicator.

A potato dextrose (PD) agar medium available from Difco was used as the medium. An sterilized pulp disc (diameter: 1 cm, manufactured by Toyo) was placed at the center of PD agar plate medium and about 3,000 spores of Trichoderma reesei IFO31329 were inoculated.

At positions by 3 cm apart from the pulp disc inoculated with spores were concentrically placed 5–6 sheets of sterilized pulp discs at the same intervals. The pulp discs were impregnated with 5–10 µg of the purified protein. The plate was incubated at 25° C. for 3–4 days and inhibition of growth of hypha around the discs containing the protein was observed under a microscope.

Figure 3A:
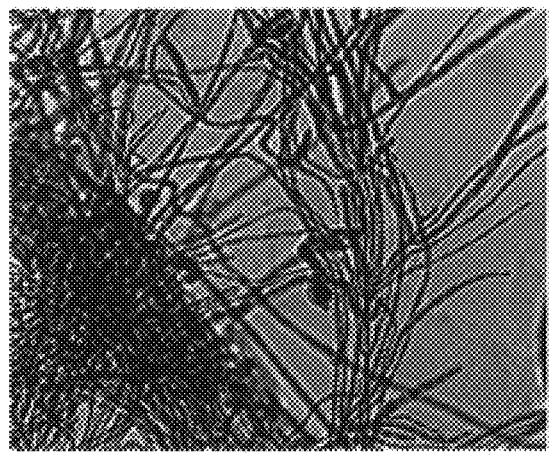
FIGS. 3A and 3B are a microscopic photograph (×100) showing a morphology of the mould for displaying antifungal activity of the purified rice chitinase.
Figure 3B:

The result is shown in FIG. 3 (micrograph, magnification:×100). As is evident from FIG. 3, the growth of the hypha of Trichoderma reesei IFO31329 was inhibited by said protein. Thus, in the Figure, A shows a control experiment in which growth of Trichoderma reesei IFO31329 around pulp discs containing bovine serum albumin was tested and in which normal extension of the hypha was observed. On the other hand, B shows an experiment in which growth of Trichoderma reesei IFO31329 around pulp discs containing the purified protein (rice chitinase) was tested and remarkable inhibition of extension of the hypha could be observed. The antifungal activity of the purified protein was proved by the above facts.

(j) Antibacterial activity of the protein

Further, for the lysozyme activity lysing cell walls of bacteria, lytic activity against Micrococcus lysodeikticus (manufactured by Sigma) was tested according to a method of Richard et al. (Richard, T. M., McCollum, T. G., Niedz, R. P., Hearn, C. J., McDonald, R. E., Berdis, E. and Doosdar, H., Planta, 200, 289–295, 1996).

Briefly, the purified protein (5 µg/5 µl) and egg white lysozyme (5 µg/5 µl) were added dropwise onto 1.5% agar plate (pH: 4.8) containing 0.03% freeze-dried cells of Micrococcus lysodeikticus. After incubating at 37° C. for 16 hours, presence or absence of plaque was checked. As the result, the purified protein showed a lytic activity same with or more than that of egg white lysozyme.

From the above-described facts, it was demonstrated that the complementary DNA of the present invention encodes a chitinase having a novel characteristic.

The entire disclosure of Japanese Patent Application No. 10-123905 filed on Apr. 20, 1998 including specification, claims and summary are incorporated herein by reference in its entirety.

What is claimed is:

1. A complementary DNA for a rice chitinase encoding a protein comprising an amino acid sequence described in SEQ ID NO: 6 in SEQUENCE LISTING.

2. A plasmid vector containing the complementary DNA for a rice chitinase according to claim 1.

3. A transformant having the plasmid vector according to claim 2.

4. The transformant according to claim 3 wherein said transformant is *E. coli* pS4960 (FERM BP-6286).

* * * * *

SEQUENCE LISTING

<160> NUMBER OF SEQ ID NOS: 6

<210> SEQ ID NO 1
<211> LENGTH: 1109
<212> TYPE: DNA
<213> ORGANISM: rice plant (Oryza sativa L. Nipponbare)
<220> FEATURE:
<221> NAME/KEY: CDS
<222> LOCATION: (29)..(946)

<400> SEQUENCE: 1

```
cggacgctga attcgatcga gaatcacc atg atg aca agt aga atg ttt tcg         52
                             Met Met Thr Ser Arg Met Phe Ser
                              1               5 gca atg cag atg ctg atc atg gtg gtg gtg gca ttg gcc ggg cta gct      100
Ala Met Gln Met Leu Ile Met Val Val Val Ala Leu Ala Gly Leu Ala
        10                  15                  20 gcc gga acg cgc gcc ggc gac atc gcg atc tac tgg ggc cag aac ggc      148
Ala Gly Thr Arg Ala Gly Asp Ile Ala Ile Tyr Trp Gly Gln Asn Gly
 25                  30                  35                  40 aac gag ggc acg ctg gcg cag acg tgc gcg acc ggt aat tac agg ttc      196
Asn Glu Gly Thr Leu Ala Gln Thr Cys Ala Thr Gly Asn Tyr Arg Phe
                 45                  50                  55 gtc atc gtg gcc ttc ctg cct gtg ttc ggc aag ggc cag acg ccg gtg      244
Val Ile Val Ala Phe Leu Pro Val Phe Gly Lys Gly Gln Thr Pro Val
             60                  65                  70
```

```
ctg aac ctg gcc ggc cac tgc gac ccg gcg tcg aac ggc tgc acc ggc      292
Leu Asn Leu Ala Gly His Cys Asp Pro Ala Ser Asn Gly Cys Thr Gly
        75                  80                  85 gtg ggc gcc gac atc aag tcg tgc cag agc ctc ggc atc aag gtc atg      340
Val Gly Ala Asp Ile Lys Ser Cys Gln Ser Leu Gly Ile Lys Val Met
    90                  95                 100 ttc tcg atc ggc ggc ggc gtc ggc aac tac ggc ctg tcc tcc cgc gac      388
Phe Ser Ile Gly Gly Gly Val Gly Asn Tyr Gly Leu Ser Ser Arg Asp
105                 110                 115                 120 gac gcc aag cag gtc gcg gcg tac ctg tgg aac aac tac ctc ggc ggc      436
Asp Ala Lys Gln Val Ala Ala Tyr Leu Trp Asn Asn Tyr Leu Gly Gly
            125                 130                 135 acg tcg ccg tca agg ccg ctc ggc gac gcc gtc atg gac ggc atc gac      484
Thr Ser Pro Ser Arg Pro Leu Gly Asp Ala Val Met Asp Gly Ile Asp
            140                 145                 150 ttc gac atc gag agc ggc ggg ggc atg tac tgg gac gac ttg gcc agg      532
Phe Asp Ile Glu Ser Gly Gly Gly Met Tyr Trp Asp Asp Leu Ala Arg
            155                 160                 165 tac ctc aag gcg tac tcg cgg cag ggg agc agc aag aag ccg gtg tac      580
Tyr Leu Lys Ala Tyr Ser Arg Gln Gly Ser Ser Lys Lys Pro Val Tyr
170                 175                 180 ctg acg gcg gcg cca cag tgc ccc ttc ccg gac gcg tcg ctc ggc gtc      628
Leu Thr Ala Ala Pro Gln Cys Pro Phe Pro Asp Ala Ser Leu Gly Val
185                 190                 195                 200 gcg ctc agc acc ggc ctg ttc gac tac gtg tgg gtg cag ttc tac aac      676
Ala Leu Ser Thr Gly Leu Phe Asp Tyr Val Trp Val Gln Phe Tyr Asn
            205                 210                 215 aac ccg ccg tgc cag tac agc tcg tcc aac ggc gtg ggc aac ctg gcg      724
Asn Pro Pro Cys Gln Tyr Ser Ser Ser Asn Gly Val Gly Asn Leu Ala
            220                 225                 230 agc gcg tgg aag cag tgg acg tcg atc ccg gcg gga cgg gtg ttc ctc      772
Ser Ala Trp Lys Gln Trp Thr Ser Ile Pro Ala Gly Arg Val Phe Leu
            235                 240                 245 ggc ctg ccg gcg gcg gcg gag gcc gcc ggc acc ggg ttc gtg gag acg      820
Gly Leu Pro Ala Ala Ala Glu Ala Ala Gly Thr Gly Phe Val Glu Thr
        250                 255                 260 agc gac ctg gtg tcg aag gtg ctc ccc gtg gtg aag aag tct ccc aag      868
Ser Asp Leu Val Ser Lys Val Leu Pro Val Val Lys Lys Ser Pro Lys
265                 270                 275                 280 tac gga ggg atc atg ctg tgg tcg cgg tac tat gac ggg ctc acg ggg      916
Tyr Gly Gly Ile Met Leu Trp Ser Arg Tyr Tyr Asp Gly Leu Thr Gly
                285                 290                 295 tac agc gac aag gtg aag tcc agc gtt tga gctagccagg gtaagctcgt       966
Tyr Ser Asp Lys Val Lys Ser Ser Val
            300                 305 gtcaggtcgg cgttcgcgta gaatcacacg tgccgcgcgt tccctgcaag atggagtagt   1026
ttctacacat ttcagaacaa agcaaacatg tacaataaga tggccggctt gtatactcat   1086
ttagaagcag aaaaaattgt gag                                          1109

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence:pS6940
<220> FEATURE:
<221> NAME/KEY: mat_peptide
<222> LOCATION: (1)..(29)

<400> SEQUENCE: 2
```
ccaccatggg cgacatcgcg atctactgg                                                29

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:pS6940
<220> FEATURE:
<221> NAME/KEY: mat_peptide
<222> LOCATION: (1)..(27)

<400> SEQUENCE: 3
aagaagcttc accttgtcgc tgtaccc                                                  27

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence:pOIS5
<220> FEATURE:
<221> NAME/KEY: mat_peptide
<222> LOCATION: (1)..(33)

<400> SEQUENCE: 4
tactacgtag gcgacatcgc gatctactgg ggc                                           33

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence:pOIS5
<220> FEATURE:
<221> NAME/KEY: mat_peptide
<222> LOCATION: (1)..(34)

<400> SEQUENCE: 5
tgcggccgct cagcggtggc agcagccaac tcag                                          34

<210> SEQ ID NO 6
<211> LENGTH: 305
<212> TYPE: PRT
<213> ORGANISM: rice plant (Oryza sativa L. Nipponbare)

<400> SEQUENCE: 6

Met Met Thr Ser Arg Met Phe Ser Ala Met Gln Met Leu Ile Met Val
  1               5                  10                  15

Val Val Ala Leu Ala Gly Leu Ala Ala Gly Thr Arg Ala Gly Asp Ile
             20                  25                  30

Ala Ile Tyr Trp Gly Gln Asn Gly Asn Glu Gly Thr Leu Ala Gln Thr
         35                  40                  45

Cys Ala Thr Gly Asn Tyr Arg Phe Val Ile Val Ala Phe Leu Pro Val
     50                  55                  60

Phe Gly Lys Gly Gln Thr Pro Val Leu Asn Leu Ala Gly His Cys Asp
 65                  70                  75                  80

Pro Ala Ser Asn Gly Cys Thr Gly Val Gly Ala Asp Ile Lys Ser Cys
                 85                  90                  95

Gln Ser Leu Gly Ile Lys Val Met Phe Ser Ile Gly Gly Val Gly
                100                 105                 110

Asn Tyr Gly Leu Ser Ser Arg Asp Asp Ala Lys Gln Val Ala Ala Tyr
            115                 120                 125

-continued

```
Leu Trp Asn Asn Tyr Leu Gly Gly Thr Ser Pro Ser Arg Pro Leu Gly
    130                 135                 140

Asp Ala Val Met Asp Gly Ile Asp Phe Asp Ile Glu Ser Gly Gly Gly
145                 150                 155                 160

Met Tyr Trp Asp Asp Leu Ala Arg Tyr Leu Lys Ala Tyr Ser Arg Gln
            165                 170                 175

Gly Ser Ser Lys Lys Pro Val Tyr Leu Thr Ala Ala Pro Gln Cys Pro
        180                 185                 190

Phe Pro Asp Ala Ser Leu Gly Val Ala Leu Ser Thr Gly Leu Phe Asp
        195                 200                 205

Tyr Val Trp Val Gln Phe Tyr Asn Asn Pro Pro Cys Gln Tyr Ser Ser
    210                 215                 220

Ser Asn Gly Val Gly Asn Leu Ala Ser Ala Trp Lys Gln Trp Thr Ser
225                 230                 235                 240

Ile Pro Ala Gly Arg Val Phe Leu Gly Leu Pro Ala Ala Ala Glu Ala
            245                 250                 255

Ala Gly Thr Gly Phe Val Glu Thr Ser Asp Leu Val Ser Lys Val Leu
            260                 265                 270

Pro Val Val Lys Lys Ser Pro Lys Tyr Gly Gly Ile Met Leu Trp Ser
        275                 280                 285

Arg Tyr Tyr Asp Gly Leu Thr Gly Tyr Ser Asp Lys Val Lys Ser Ser
    290                 295                 300

Val
305
```